United States Patent [19]
Faupel et al.

[11] Patent Number: 5,320,101
[45] Date of Patent: Jun. 14, 1994

[54] DISCRIMINANT FUNCTION ANALYSIS METHOD AND APPARATUS FOR DISEASE DIAGNOSIS AND SCREENING WITH BIOPSY NEEDLE SENSOR

[75] Inventors: Mark L. Faupel, Conyers, Ga.; G. A. P. Ganepola, Hillsdale, N.J.

[73] Assignee: Biofield Corp., New York, N.Y.

[21] Appl. No.: 859,170

[22] Filed: Mar. 27, 1992

Related U.S. Application Data

[60] Continuation-in-part of Ser. No. 579,970, Sep. 10, 1990, Pat. No. 5,099,844, which is a division of Ser. No. 288,572, Dec. 22, 1988, Pat. No. 4,995,383.

[51] Int. Cl.$^5$ .................. A61B 5/00; A61B 10/00
[52] U.S. Cl. .................. 128/653.1; 128/642; 128/734; 128/753; 128/754
[58] Field of Search .................. 128/653.1, 639, 642, 128/734, 749, 753, 754, 763, 635

[56] References Cited

U.S. PATENT DOCUMENTS

| | | | |
|---|---|---|---|
| 3,313,293 | 4/1967 | Chesebrough et al. | 128/642 |
| 3,568,662 | 3/1971 | Everett et al. | 128/642 |
| 3,971,366 | 7/1976 | Motoyama | 128/639 |
| 4,170,225 | 10/1979 | Criglar et al. | 128/733 |
| 4,263,920 | 4/1981 | Tasto et al. | 128/734 |
| 4,275,743 | 6/1981 | Hjort | 128/731 |
| 4,291,708 | 9/1981 | Frei et al. | 128/734 |
| 4,328,809 | 5/1982 | Hirschowitz et al. | 128/653.1 |
| 4,407,300 | 10/1983 | Davis | 128/734 |
| 4,416,288 | 11/1984 | Freeman | 128/731 |
| 4,486,835 | 12/1984 | Bai et al. | 364/414 |
| 4,499,901 | 2/1985 | Chang et al. | 128/635 |
| 4,557,271 | 12/1985 | Stoller et al. | 128/734 |
| 4,557,273 | 12/1985 | Stoller et al. | 128/738 |
| 4,936,306 | 6/1990 | Doty | 128/642 |
| 4,955,383 | 9/1990 | Faupel | 128/653.1 |
| 4,969,468 | 11/1990 | Byers et al. | 128/642 |
| 5,099,844 | 3/1992 | Faupel | 128/653.1 |
| 5,143,079 | 9/1992 | Frei et al. | 128/734 |

FOREIGN PATENT DOCUMENTS

| | | |
|---|---|---|
| 0050353 | 4/1982 | European Pat. Off. |
| 0320109 | 6/1989 | European Pat. Off. ............ 128/635 |

OTHER PUBLICATIONS

European Surgical Research, 1990, Measurement of the Electrical Bio-Impedance of Breast Tumors, T. Morimoto, Y. Kinouchi, T. Iritani, S. Kimura, Y. Konishi, N. Mitsuyama, K. Komaki, Y. Monden, vol. 22, pp. 86–92.

*Primary Examiner*—Lee S. Cohen
*Assistant Examiner*—K. M. Pfaffle
*Attorney, Agent, or Firm*—Sixbey, Friedman, Leedom & Ferguson

[57] ABSTRACT

A biopsy method and apparatus for determining and locating the presence or absence of a neoplastic and other disease condition within a human or animal subject by detecting during a test period the respective electrical potentials of the electromagnetic field present in the subject between each of a plurality of measurement locations in the area of the neoplasm and at least one reference location while a combination biopsy instrument and electrode is inserted into the subject at the location of suspected neoplasm. Electrical potential differences are compared during this period to obtain relationships therebetween which are indicative of either the presence or absence of neoplastic tissue. Once the neoplastic tissue is located and identified, the biopsy instrument is manipulated to remove a tissue sample for further study.

18 Claims, 5 Drawing Sheets

DISCRIMINANT FUNCTION ANALYSIS METHOD AND APPARATUS FOR DISEASE DIAGNOSIS AND SCREENING WITH BIOPSY NEEDLE SENSOR

This application is a continuation-in-part application of Ser. No. 07/579,970, filed Sep. 10, 1990 now U.S. Pat. No. 5,099,8 which is a divisional application of Ser. No. 07/288,572 filed Dec. 22, 1988, now U.S. Pat. No. 4,995,383.

TECHNICAL FIELD

The present invention relates generally to a method and apparatus for diagnosing, screening or sensing disease states, particularly the existence of neoplastic tissue in a living organism by detecting the potential of the electromagnetic field present between a reference and one or more test points on or within the living organism to measure the gradient of electrical activity which occurs as a function of biological activity.

BACKGROUND ART

In recent years the theory that measurement of the potential level of the electromagnetic field of a living organism can be used as an accurate diagnostic tool is gaining greater acceptance. Many methods and devices have been developed in an attempt to implement this theory. For example, U.S. Pat. No. 4,328,809 to B. H. Hirschowitz et al deals with a device and method for detecting the potential level of the electromagnetic field present between a reference point and a test point of a living organism. Here, a reference electrode provides a first signal indicative of the potential level of the electromagnetic field at the reference point, while a test electrode provides a second signal indicative of the potential level of the electromagnetic field at the test point. These signals are provided to an analog-to-digital converter which generates a digital signal as a function of the potential difference between the two, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al patent contemplates the use of a plurality of test electrodes, while U.S. Pat. Nos. 4,416,288 to Freeman and 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and devices which implement them operate on the basis that a disease state is indicated by a negatize polarity which occurs relative to a reference voltage obtained from another site on the body of a patient, while normal or nonmalignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnostic inaccuracy, particularly where only surf ace measurements are taken.

First, the polarity of diseased tissue underlying a recording electrode has been found to change over time. This fact results in a potential change which confounds reliable diagnosis when only one external recording electrode is used. Additionally, the polarity of tissue is measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). once this fact is recognized, it follows that important electrical indications of disease are going to be seen in the relative voltages recorded from a number of sites at and near a diseased area, and not, as previously assumed, on the direction (positive vs. negative) of polarity.

Once the location of a disease state, such as suspected neoplastic tissue or cancer, has been identified, the conventional diagnostic approach has been to perform a biopsy so that the diseased tissue could be examined to confirm the diagnosis. During this procedure a needle is inserted from outside the patient's body into the suspected neoplasm or other diseased tissue to permit the removal of a sample for a pathology study. To insure the accurate insertion of the needle into the diseased tissue to be biopsied, it has been necessary to employ radiographic techniques which allow the practitioner to see the neoplasm and view the biopsy needle during insertion. Even then, it is not always a certainty that the needle has reached the neoplasm, and a method of confirming this to augment radiographic techniques would be beneficial.

Biopsy procedures are perferably performed in a surgical suite, an operating room or other area that is sterile as possible. If the pathology report indicates the need for immediate surgery, it is diserable for the patient to be near surgical facilities. In many cases patients have had to be moved from the radiology area to the surigical suite with the biopsy needle in place because the necessary radiology equipment for positioning the needle was located only in the radiology area.

There is a need, therefore, for a discriminant analysis method and apparatus which not only externally diagnoses and screens disease sites, but which also internally identifies and locates diseased tissue, particularly neoplastic tissue so that the appropriate further diagnostic and treatment steps may be taken.

DISCLOSURE OF THE INVENTION

It is a primary object of the present invention to provide a novel and improved biopsy method and apparatus for providing disease diagnosis and particularly for cancer diagnosis. Such method and apparatus operate to determine the relationships between a set of voltages taken internally from the area of a disease site within a living organism.

Another object of the present invention is to provide a novel and improved biopsy method and apparatus for the discriminant analysis of a disease site within a living organism wherein voltage potentials are measured in the area of the disease site over time. A maximum voltage differential is obtained from an average of multiple readings taken over time which constitutes a minimum voltage that is subtracted from a maximum voltage where two or more electrodes are recording voltages simultaneously or concurrently from a specific disease site or organ.

A further object of the present invention is to provide a novel and improved biopsy method and apparatus for providing an indication of the location of a biopsy needle relative to neoplastic tissue for cancer diagnosis. Relative voltages are recorded from a number of internal sites near a disease area using a combination biopsy needle and electrode as the needle electrode is inserted through tissue into a cancerous lesion. Signal measurements taken from such sites are used to locate the biopsy needle precisely in the neoplastic tissue to permit a biopsy to be taken.

A still further object of the present invention is to provide a novel and improved biopsy method and apparatus involving discriminant analysis to facilitate the accurate location of a disease site and the placement of biopsy instruments for cancer diagnosis. Recordings at or near suspected neoplastic tissue are taken and the voltage levels recorded are analyzed in terms of a discriminant mathematical analysis to locate the site of a possible malignancy. Additional voltage measurements are taken as a biospy instrument is inserted through tissue toward the disease site to position a biopsy instrument accurately within the neoplastic tissue without external visual aids, such as radiography. The aim of the method and apparatus is to measure the gradient of electrical activity which occurs as a function of the biological activity of the specific organ system.

BEST MODE FOR CARRYING OUT THE INVENTION

Figure 1:
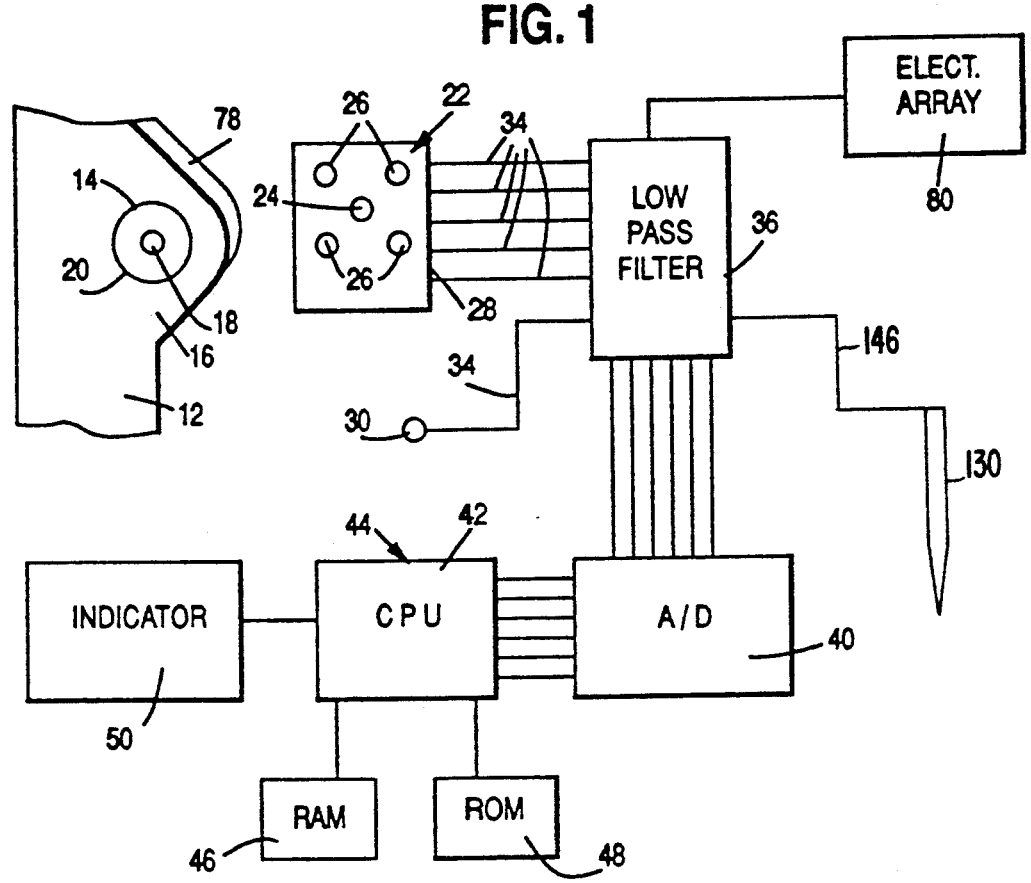
FIG. 1 is a block diagram of the apparatus of the present invention.
Figure 2:
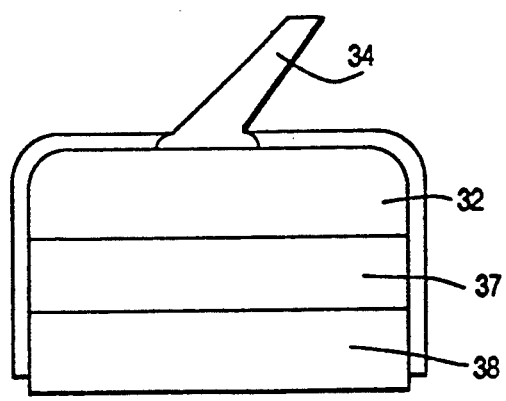
FIG. 2 is a cross-sectional diagram of an electrode for the apparatus of FIG. 1.

FIG. 1 discloses a basic block diagram of the apparatus of the present invention indicated generally at 10 for performing a discriminant analysis for disease screening or diagnosis. For purposes of illustration, the apparatus 10 will be described in connection with methods involving the screening for, or diagnosing of breast cancer. However, it should be recognized that the method and apparatus of the invention can be similarly employed for screening or diagnosis at other disease sites involving other portions or organs of a living human or animal.

In FIG. 1, a human subject 12 may have a cancerous lesion 14 on one breast 16. This cancerous lesion has a core 18 and an outer zone 20 surrounding the core where various differing local effects, such as changes in vascularization, water content and cell division rate occur. Assuming first, for purposes of discussion, that the location of the lesion 14 is not known, and the device 10 is to be used to screen the breast 16 to determine whether or not a disease condition exists, skin surface potentials will be measured in an area of the breast, including the zone 20 using an electrode array 22. In FIG. 1, the electrode array includes a central electrode 24 surrounded by four periperal electrodes 26. However, the device and method of this invention contemplate the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. For breast cancer screening (where patients are asymptomatic) the array should give maximum coverage of the entire breast surface. The aim in both of these cases is to measure the gradient of electrical activity which occurs as a function of the underlying biological activity of the organ system. The number of electrodes used in the measurement will also be a function of specific application, and breast cancer screening may require the use of as few as twelve or as many as forty or more electrodes for each breast, while in screening for prostate cancer, as few as two measurement electrodes might be used.

The core electrode 24 and the peripheral electrodes 26 are mounted upon a flexible backing sheet 28 which permits the electrodes to be positioned against the curved surface of the breast 16 while still maintaining the position of the electrodes in a predetermined pattern. However, other electrode arrays may be employed wherein each individual electrode can be individually positioned, and the relative position between electrodes can be altered. The electrode array 22 is used in conjunction with a reference electrode 30, and all of these electrodes may be of a known type used for detecting the potential level of the electromagnetic field present in a living organism. Ideally, the electrodes 24, 26 and 30 should be of a type which do not cause a substantial battery effect between the organism under test and the electrode. A common electrode suitable for use as the electrodes 24, 26 and 30 is illustrated in FIG.

2, and includes a layer of silver 32 having an electrical lead 34 secured in electrical contact therewith. In contact with the silver layer 32 is a layer 37 of silver chloride, and extending in contact with the silver chloride layer is a layer of bridging material 38, such as sodium chloride, which contacts the surface of a living organism.

The device 10 is a multi-channel device having electrode leads 34 extending separately from the central electrode 24, the peripheral electrodes 26, and the reference electrode 30 to a low pass filter 36. This filter operates to remove undesirable high frequency AC components which appear on the slowly varying DC voltage signal outputs provided by each of the electrodes as a result of the electromagnetic field measurement. The low pass filter 36 may constitute one or more multiple input low pass filters of known type which separately filter the signals on each of the input leads 34 and then pass each of these filtered signals in a separate channel to a multiple input analog-to-digital converter 40. Obviously, the low pass filter 36 could constitute an individual low pass filter for each of the specific channels represented by the leads 34 which would provide a fillering action for only that channel, and then each filtered output signal would be connected to the input of the analog-to-digital converter 40.

The converter 40 is a multiple input multiplex analog-to-digital converter of a known type, such as that manufactured by National Semiconductor, Inc. and designated as ADC808. For multiple channels, it is possible that more than one multiple input analog-to-digital converter will be used as the converter 38. For example, if an 8-input analog-to-digital converter is used and there are 24 input and output channels from the low pass filter 36, then the analog-to-digital converter 38 might include three 8-input converters.

The analog-to-digital converter 38 converts the analog signal in each input channel to a digital signal which is provided on a separate output channel to the multiple inputs of a central processing unit 42. The central processing unit is a component of a central control unit indicated generally at 44 which includes RAM and ROM memories 46 and 48. Digital input data from the analog-to-digital converter 40 is stored in memory and is processed by the CPU in accordance with a stored program to perform the diagnostic and scanning methods of the present invention. The information derived by the CPU as a result of this processing is then fed to a suitable indicator device 50 which may constitute a printer, a CRT display device, or a combination of such conventional indicators.

The operation of the discriminant analysis device 10 will be clearly understood from a brief consideration of the broad method steps of the invention which the device is intended to perform. When the lesion 14 has not been identified and a screening operation is performed to determine whether or not a lesion is present, a screening electrode array 22 is positioned in place with the central- electrode 24 in the center of the site being screened and the peripheral electrodes 26 over various diverse areas of the site. If a breast 16 is screened, the electrode array may cover either the complete breast or a substantial area thereof. The reference electrode 30 is then brought into contact with the skin of the subject 12 in spaced relationship to the electrode array 22, and this reference electrode might, for example, be brought into contact with a hand of the subject. Then, the electromagnetic field between the reference electrode and each of the electrodes 24 and 26 is measured, filtered, converted to a digital signal and stored for processing by the central processing unit 42. The program control for the central processing unit causes a plurality of these measurements to be taken over a period of time, and the measurement son all channels may be taken simultaneously and repetitively for the predetermined measurement time period. Alternatively, sequential measurements between the reference electrode and one of the electrodes 24 and 26 can be taken until each channel is sampled, and then the sequential measurement is repeated for the predetermined measurement period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the central processing unit 42 at the end of the measurement period. For the duration of a single predetermined measurement period, with five measurement channels as shown, the central processor will obtain five average signals indicative of the average electromagnetic field for the period between the reference electrode 30 and each of the electrodes in the electrode array 22.

Having once obtained an average signal level indication as measured by each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of more serious disease, while a different subset might be obtained which will be indicative of the absence of serious disease. Although a number of methods and decision making logic may be designed to obtain and analyze the relationships between the average potential values in accordance with this invention for screening or diagnostic purposes, the discriminant mathmatical analysis procedure to be hereinafter described is a method which appears to be effective.

The most important relationship which may be obtained is designated the maximum voltage differential (MVD), which is defined as the minimum average voltage value obtained during the measurement period subtracted from the maximum average voltage value obtained for the same period where two or more electrodes are recording voltages from a lesion. Thus, for each predetermined measurement period, the lowest average voltage level indication obtained on any of the channels is subtracted from the highest average voltage level indication obtained on any one of the channels to obtain an MVD voltage level. If this MVD voltage level is above a desired levels $>x$, for example, 20.0 mV, then a disease condition, such as a maligancy, may be indicated. Similarly, if the average taken over the measurement period from one channel is an abnormally low value $<y$, for example below 5.0 mV, then a disease condition, such as malignancy may also be indicated. Thus, in accordance with the present method, an abnormally low individual electrode reading (IER) or an abnormally high MVD are used to provide an indication of the existence of a disease condition. These primary indicators may be further analyzed in accordance with a control program to be subsequently described to reduce the number of false positive diagnoses, usually cases of non-malignant hyperplasia which may be falsely identified as cancer on the basis of high MVD or low IER readings.

When the device 10 is used in accordance with the method of the present invention for a screening function where a specific lesion 14 has not yet been identified, using as an example breast screening where the patient is asymptomatic, an array 22 is employed which will give maximum coverage of the entire breast surface. Then MVD levels and IER levels are obtained in accordance with the method previously described.

Figure 3:
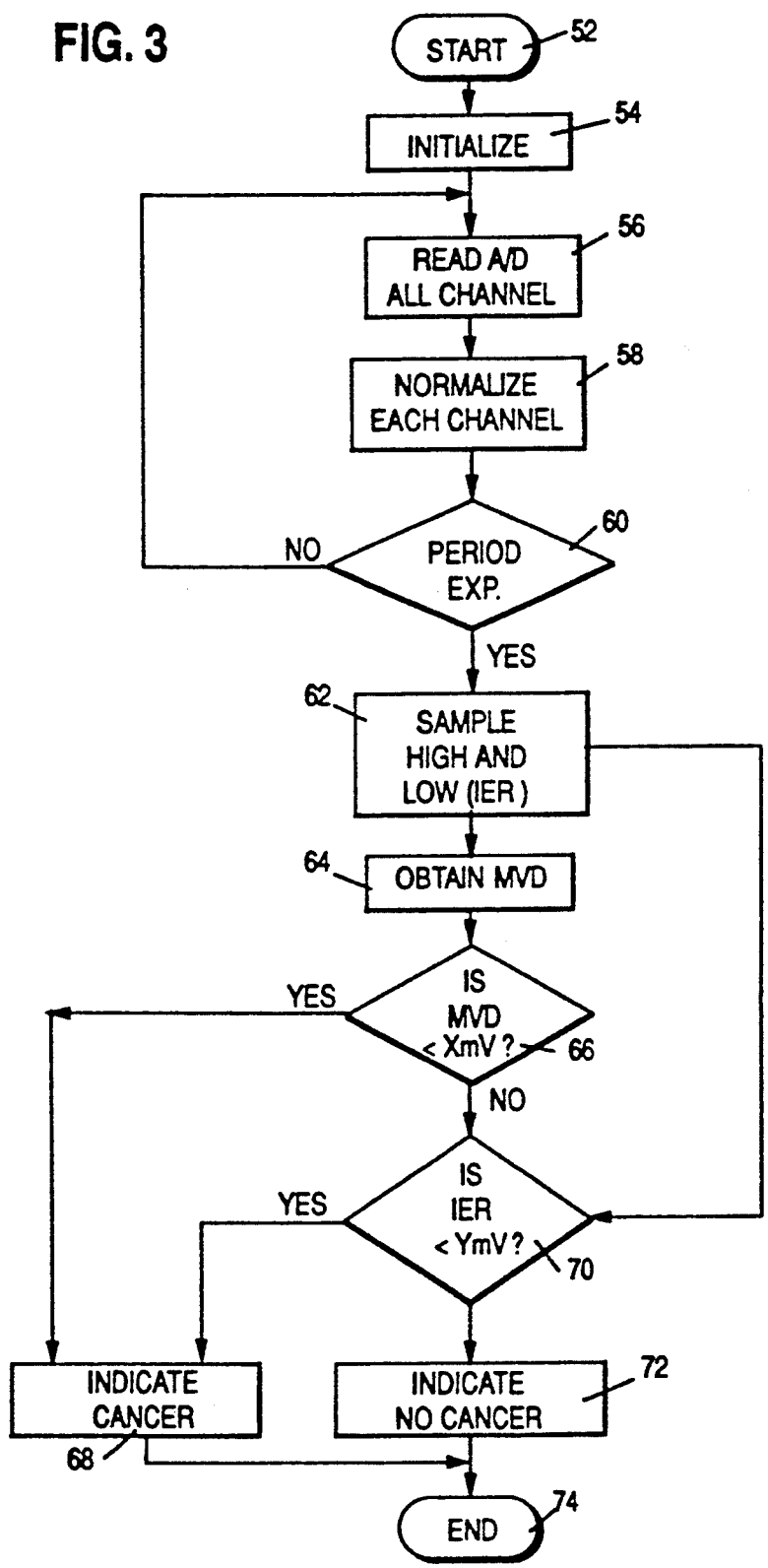
FIG. 3 is a flow diagram of the measurement operation of the apparatus of FIG. 1 used to obtain a maximum voltage differential and a low individual channel value.

The general overall operation of the central processor unit 42 will best be understood with reference to the flow diagram of FIG. 3. The operation of the unit 10 is started by a suitable start switch as indicated at 52 to energize the central processing unit 42, and this triggers an initiate state 54. In the initiate state, the various components of the device 10 are automatically brought to an operating mode, with for example, the indicator 50 being activated while various control registers for the central processing unit are reset to a desired state. Subsequently, at 56, a predetermined multiple measurement period is initiated and the digital outputs from the analog-to-digital converter 40 are read. The central processing unit may be programmed to simultaneously read all channel outputs from the analog-to-digital converter, or these channel outputs may be sequentially read.

Once all channels from the analog-to-digital converter are read, an average signal for each channel is obtained at 58 for that portion of the measurement period which has expired. The average or normalized value for each channel is obtained by summing the values obtained for that channel during the measurement period and dividing the sum by the number of measurements taken. Then, at 60, the central processor unit determines whether the measurement period has expired ana the desired number of measurements have been taken and if not, the collection of measurement samples or values continues.

Once the measurement period has expired, the microprocessor will have obtained a final average value for each channel derived from the measurements taken during the span of the measurement period. From these average values, the highest and lowest average values obtained during the measurement period are sampled at 62, and at 64, and the lowest average channel value which was sampled at 62 is subtracted from the highest sampled channel value to obtain a maximum voltage differential value.

The maximum voltage differential value is analyzed at 66 to determine if the value is greater than a predetermined level ($\times$my). If the maximum voltage differential is above the predetermined level, the existence of a disease condition is indicated at 68, but if it is not, then the lowest average channel output IER from 62 is analyzed at 70 to determine if this value is lower than a predetermined value y. If it is determined at 70 that the IER value is not lower than the predetermined value, then no disease condition is indicated at 72. On the other hand, if the IER value is lower than the predetermined value, then the presence of a disease condition is indicated at 68. After the indication of the presence or nonpresence of disease at 68 or 72, the routine is ended at 74.

Operation of the device 10 in accordance with the flow diagram of FIG. 3 for screening, provides a good indication of whether or not a disease condition is present in the area screened, and this simplified mode of operation may be used effectively for general screening purposes.

When a lesion 14 has been identified and located by screening in accordance with this invention or by other methods, a diagnosis is required to determine whether or not the lesion is malignant. For diagnostic purposes, the electrode array 22 is positioned in place with the central electrode 24 over the lesion core 18 and the peripheral electrodes 26 over various diverse areas of the outer zone 20 as well as over relatively normal tissue beyond but near the outer zone. The reference electrode 30 is then brought into contact with the skin of the subject 12 in spaced relationship to the electrode array 22, and again, for a breast malignancy diagnosis, this reference electrode might, for example, be brought into contact with a hand of the subject 12. Then, the electromagnetic field between the reference electrode and each of the electrodes 24 and 26 is measured, filtered, converted to a digital signal and stored for processing by the central processing unit 42. The central processing unit processes these signals in the same manner as previously described in connection with FIG. 3, but the operation exemplified by the flow diagram of FIG. 3 has no provision for the reduction of the number of false positive diagnoses which may be obtained from such conditions as nonmalignant hyperplasia and which can be falsely identified as cancer on the basis of high MVD levels or low IER levels. To reduce the occurrence of these false positives, the expanded flow diagram of FIGS. 4 and 5 is employed for diagnostic purposes where greater accuracy is required.

Figure 4:
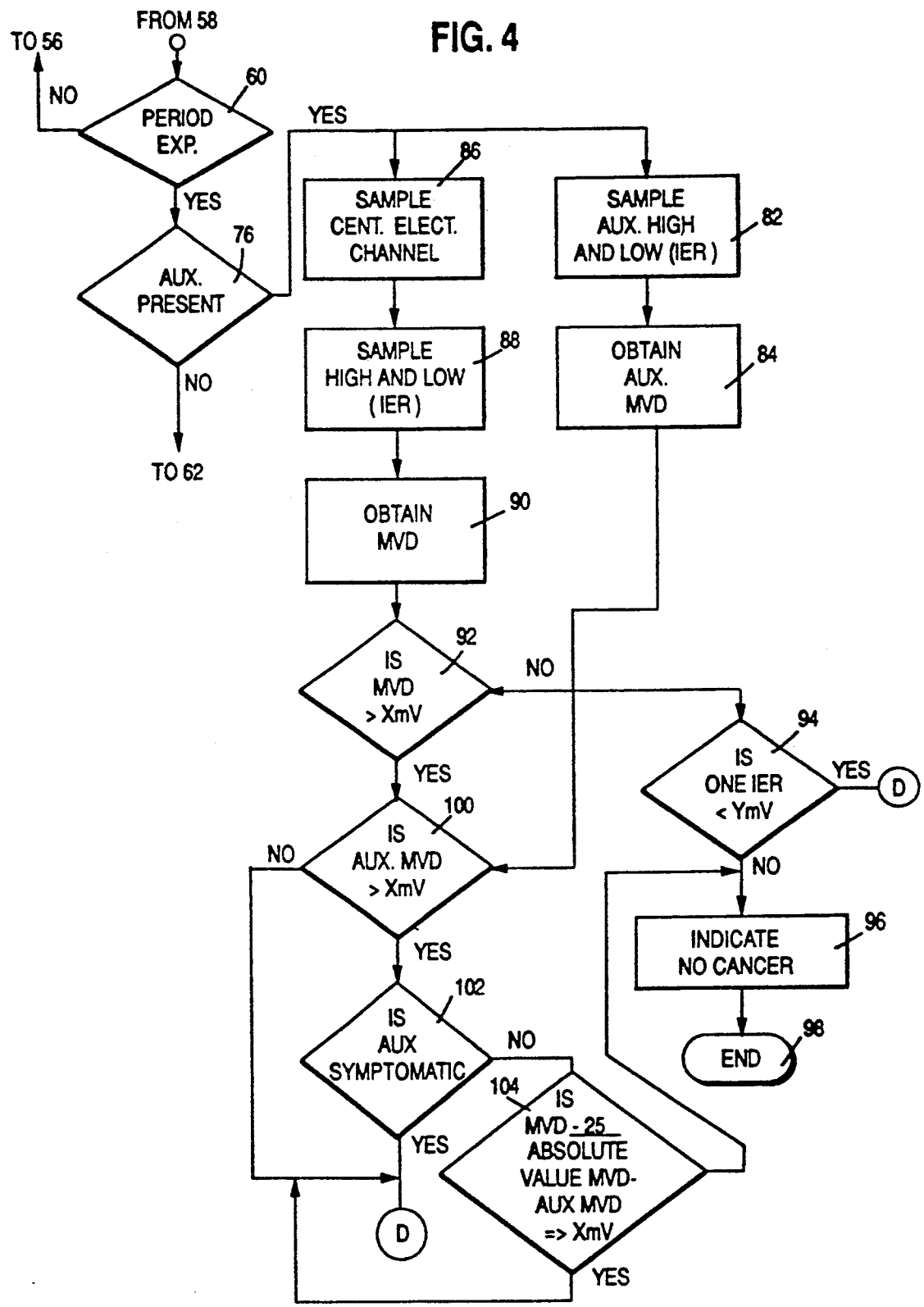
FIG. 4 is a flow diagram of the disease decision analysis provided by the apparatus of FIG. 1.
Figure 5:
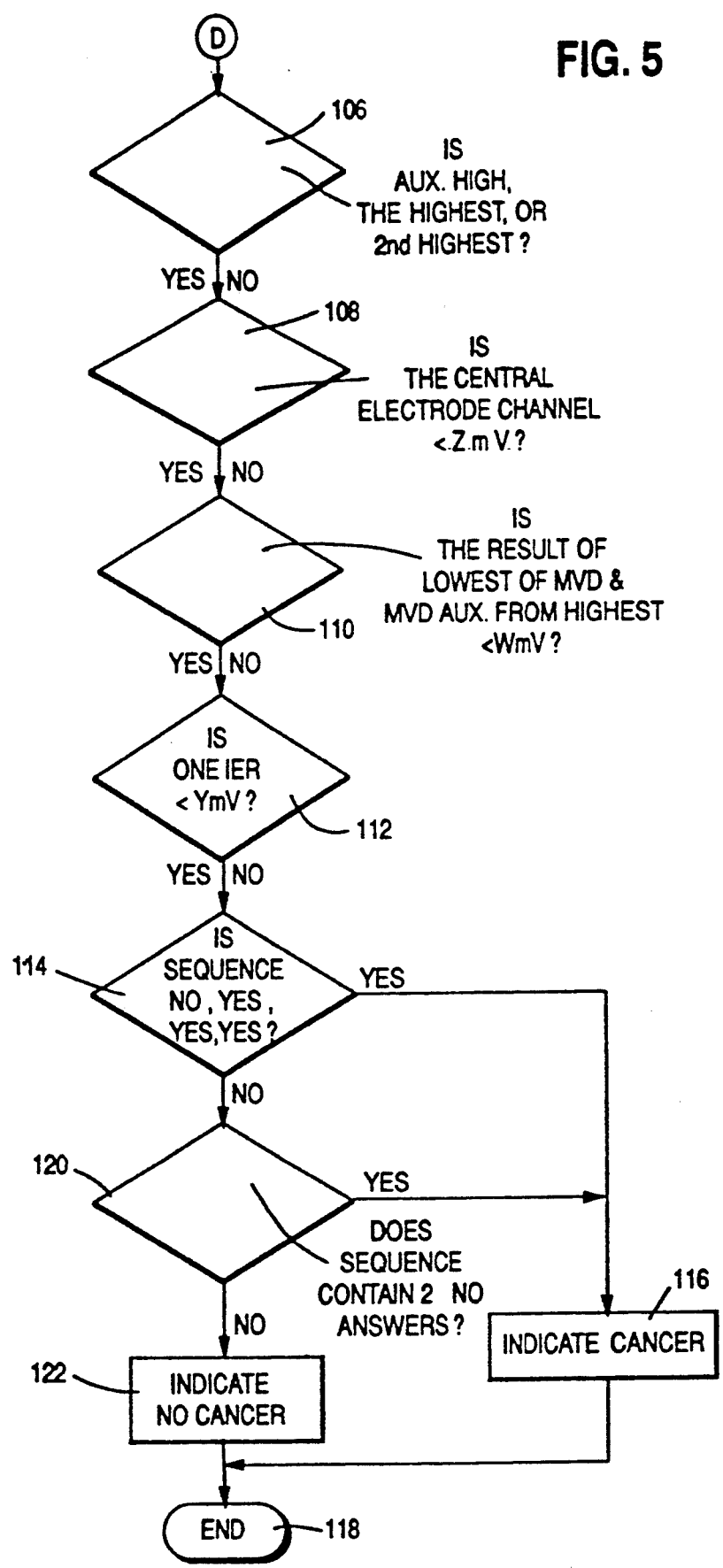
FIG. 5 is a flow diagram of an auxiliary decision sequence used with the flow diagram of FIG. 4.

Referring now to FIG. 4, the initial portion of the flow diagram of FIG. 3 down to the determination of the expiration of the measurement period at 60 is incorporated by reference. Once the measurement period expires, the system operates at 76 to determine if auxiliary measurements are present. If such auxiliary measurements are not present, then the flow diagram passes on to the sampling process 62 of the flow diagram of FIG. 3 and continues on through this flow diagram which is incorporated by reference.

On the other hand, if auxiliary measurements are sensed, then the flow diagram of FIG. 4 proceeds with an analysis of the primary measurement channels as well as the auxiliary measurement channels. To understand the source of the auxiliary measurements, it can be noted from FIG. 1 that multiple measurements can be taken and averaged f rom a symptomatic organ, such as the breast 16 and also from a similar asymptomatic or symptomatic organ such as the opposite breast 78. The measurements obtained from the breast 78 and from the core electrode 24 can form the auxiliary channel measurements, while those obtained from the breast 16 form the primary channel measurements. The auxiliary channel measurements may be taken sequentially after the primary channel measurements, or alternatively, may be taken simultaneously by using a second electrode array 80. The primary and secondary channels would be separated as they pass through the low pass filter 36 and analog-to-digital converter 40 to the central processing unit 42, but otherwise the measurements and averaging would occur for the auxiliary channels in exactly the same manner as previously described in connection with the primary channels.

Returning to FIG. 4, if the presence of auxiliary channels are sensed at 76, then the high and low auxiliary channel values are determined at 82, and a maximum voltage differential for the auxiliary channel high and low values is determined at 84. At the same time, the average value for the channel dedicated to the central electrode 24 is determined at 86 and the high and low average channel values for the primary measurement channels are determined at 88. Then at 90, the maximum voltage differential for the primary measurement channels is determined and at 92 a decision is made as to whether or not the primary measurement channel maximum voltage differential exceeds a predetermined voltage x.

As in the case of the flow diagram of FIG. 3, if the predetermined voltage x is not exceeded by the primary channel maximum voltage differential at 92, then at 94 a determination is made as to whether there is at least one low average value for the primary measurement channels which is less than a predetermined voltage level y. If there is, then the decision making logic of FIG. 5 comes into operation, but if there is not, then a NO CANCER indication is provided at 96 and the routine ends at 98.

Should the determination at 92 show that the primary channel maximum voltage differential is greater than the predetermined value x, then at 100, a determination is made as to whether or not the auxiliary channel maximum voltage differential is greater than x. If the auxiliary channel maximum voltage differential is less than x, then the decision sequence of FIG. 5 is instituted. On the other hand, if this auxiliary maximum voltage differential is greater than x, then a decision is made at 102 as to whether or not the second breast 78 is symptomatic or asymptomatic. If this breast is symptomatic, then the decision logic flow diagram of FIG. 5 is instituted, but if the breast is not symptomatic, then an equation at 104 is performed. Basically, the equation at 104 determines whether the primary channel maximum voltage differential minus 25 divided by the absolute value of the primary channel maximum voltage differential minus the auxiliary channel multiple voltage differential is equal to a value greater than the predetermined value X. If it is, then the decision sequence flow diagram of FIG. 5 is instituted, but if it is not, then a NO CANCER indication is provided at 96 and the routine is terminated at 98.

Turning now to FIG. 5, the decision sequence flow diagram involves initially answering a sequence of four questions indicated at 106, 108, 110 and 112. These questions are answered using the data obtained from the operation in accordance with the flow diagram of FIG. 4. At 106, a determination is made as to whether or not the highest average value obtained from the auxiliary channel is the highest or second highest value obtained from all channels. Then, at 108, a determination is made as to whether or not the central electrode channel value is less than a predetermined value z. After this determination, a determination is made at 110 as to whether or not the disparity between the maximum voltage differential from the primary channel and the maximum voltage differential from the auxiliary channel is less than a predetermined value w.

The final sequential question is a determination as to whether at least one average value for a channel (IER) is less than y. Once this sequence of questions has been answered, then at 114 a determination is made as to whether the sequence of answers is "no", "yes", "yes". If this sequence of answers is present, then CANCER is indicated at 116 and the routine is ended at 118.

Conversely, if the proper sequence of answers is not found at 114, then at 120 it is determined whether or not the sequence of answers contains two "no" answers. If it does, then CANCER is indicated at 116 and the routine is terminated at 118, but if it does not, then an indication of NO CANCER is provided at-122 and the routine is terminated at 118.

The control program represented by the flow diagrams of FIGS. 3–5 can be altered to preset values of w, x, y and z which are found to be most effective for a diagnosed condition. For breast cancer diagnosis, the following values have been effectively used:

w 10 mV
x 20 mV
y 5 mV
z 42 mV

The device 10 and method of the present invention operating in accordance with the flow diagrams of FIGS. 4 and 5 have been tested on 102 women with suspicious breast lesions. A correct diagnosis of CANCER was obtained in all 39 cases where cancer was verified by biopsy (there were no false negatives). It is also noteworthy that the percentage of false positives was less than 14%, a result which exceeds that of the more traditional methods of attempting to identify cancer on the basis of electronegative polarity.

Figure 6:
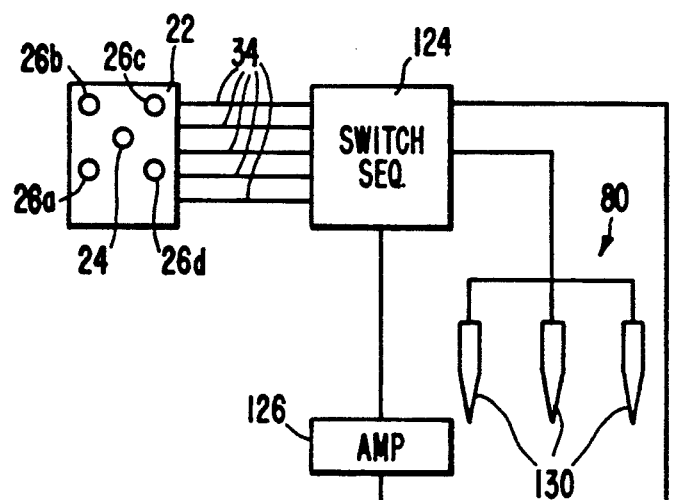
FIG. 6 is a block diagram of a second embodiment of the apparatus of the present invention.

The discriminant analysis device of the present invention may be constructed to sequentially sample the output from each electrode 26 and provide sampled potentials over a single one amplifier channel. A sequential system of this type is shown in FIG. 6 where the outputs from the electrodes 24 and 26 are fed to a switching sequencer 124 which operates under the control of the central processor 42. The central processor causes the switching sequencer to sequentially provide the outputs from specific electrodes in sequence to an amplifier 126 and the low pass filter 36. Thus, a single amplifier and a single channel to the filter 36 handle all of the outputs from the electrode array 22, and also the electrode array 80 when this array is used.

When the switching sequencer 124 is provided under the control of the central processor 42, the reference electrode 30 may well be eliminated and an electrode in either the electrode array 80 or the electrode array 22 may function as the reference electrode. This is often advantageous, as it will place the reference electrode closer to the disease site and will substantially reduce or eliminate the effects of long term drift which occur when the reference electrode is remote from the disease site. Also, this provides great flexibility in measurement technique. For example, a single electrode in either the array 80 or the array 22 can be chosen as the reference electrode for all measurements taken during a measurement period. On the other hand, the sequencer could chose different reference electrodes during the measurement period to provide measurements from different test and reference electrode combinations. In a sequential measurement operation, the sequencer could choose the electrode 26a of FIG. 6 as the reference for taking a measurement with the electrode 26b as the test electrode, and then the electrode 26b could be sequenced to become the reference electrode while a measurement is taken with the electrode 26c. This sequence can continue using all electrodes or selected electrodes in the matrix during the test period. The electrodes in both arrays 22 and 80 can be sequenced to obtain measurements from a variety of reference and test electrode combinations.

Once a disease site or suspected neoplastic tissue has been located using the external, non-evasive method and apparatus previously described or by other means, additional diagnostic procedures can be performed directly on the diseased tissue itself to determine specifically the nature of the disease state so that a suitable treatment can be selected. These additional diagnostic procedures often require obtaining a sample of the diseased tissue for evaluation. Heretofore, once the presence of a potential neoplasm was identified by external diagnostic procedures such as radiography, a tissue sample would be taken by a needle biopsy. The only way to insure that the needle was inserted accurately into the neoplastic tissue was to view the insertion using an X-ray camera. Such procedures are typically performed in the radiology section of a hospital or other health care facility, and if this occurs, the patient then must be moved to an operating room or other surgical area, often with the biopsy instrument in place. With the present invention, however, a biopsy needle or other instrument may be accurately and prescisely inserted directly into the neoplastic or diseased tissue without the need for X-rays or other visual monitoring equipment, or when such equipment is used, the present invention will provide a confirmation that the needle is properly located for a biopsy.

In accordance with the present invention, an electrode 130 (FIG. 7) is provided which is preferably configured like a conventional biopsy needle so that a single instrument performs the functions of both an electrode and a biopsy needle. However, any configuration which allows the electrode 130 to be inserted into diseased tissue from outside a patient's body with substantially no damage to healthy tissue so that a sample of diseased tissue may be removed is intended to be encompassed by the present invention. The electrode 130 is used in conjunction with a reference electrode 30 to take measurements in the manner previously described.

Figure 7:
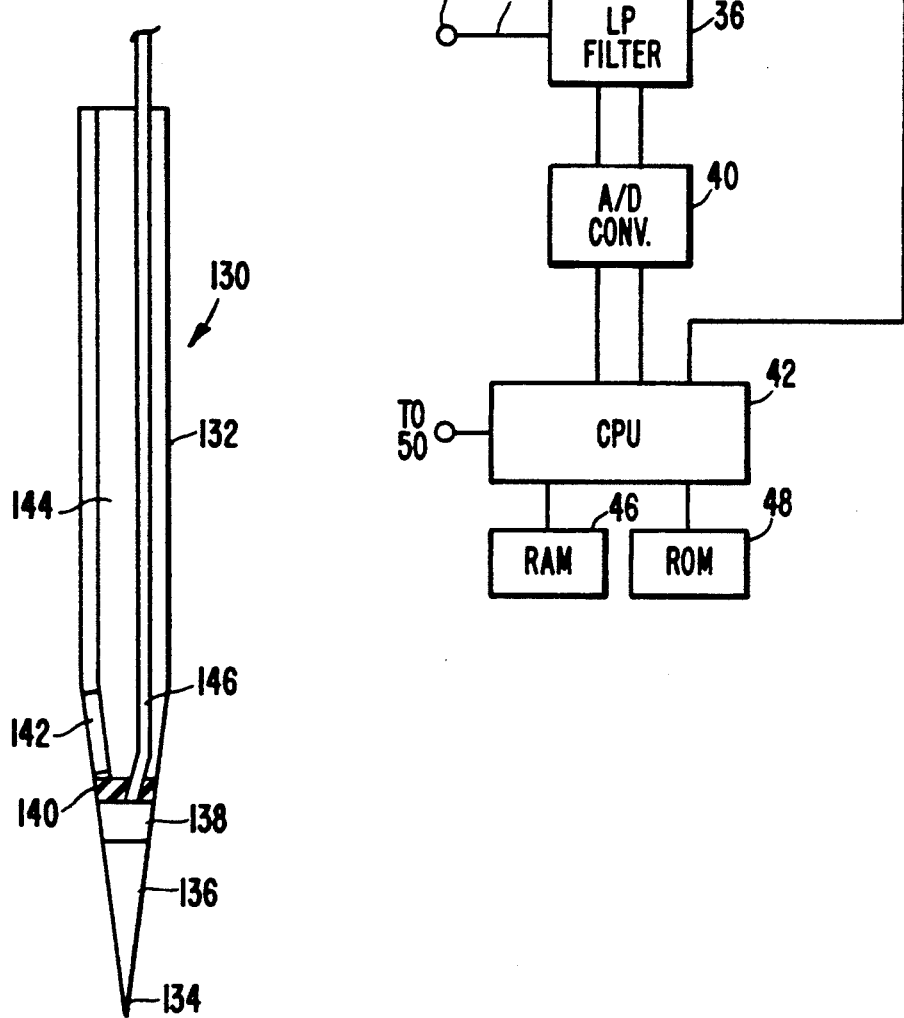
FIG. 7 is a cross sectional diagram of a biopsy needle electrode used with the present invention.

FIG. 7 illustrates a combination electrode and biopsy needle 130 having an elongate body 132 which terminates at one end with a pointed tip 134. This tip is formed from a layer of silver chloride 136 in contact with a layer of silver 138, and these layers are electrically insulated from the remainder of the body 132 by an insulation layer 140. As is typical with biopsy needles, an opening 142 in the body 132 communicates with a central channel 144 extending from the opening longitudinally through the body to facilitate the passage of a sample of diseased tissue to be removed by the biopsy needle. The upper end of the channel 144 may be connected to a source of suction, or the needle may be otherwise configured in known manner to retain and remove a tissue sample.

An electrical lead 146 is electrically connected at one end to the silver layer 138 and passes through the insulation layer 140 and the channel 144 to the exterior of the needle. This lead, as illustrated in FIG. 1, is connected to the low pass filter 36 and to one channel from the low pass filter to the analog-to-digital converter 40 and the central processing unit 42.

The combination biopsy needle and electrode 130 of the present invention is an especially effective and accurate locator of neoplatic tissue, for a relatively constant electrical potential difference between the reference electrode 30 and the needle electrode 130 will be observed before the needle electrode approaches neoplastic tissue. Once the neoplastic tissue is reached, the potential will increase or decrease indicating that the tip of the needle is accurately located in the neoplastic tissue. A plurality of measurements are taken as the needle electrode 130 advances through normal tissue toward the neoplastic tissue, and the result of these measurements is observed on the indicator 50. For purposes of these measurements, the needle electrode 130 operates in the same manner as one of the electrodes 26. Measurements may be taken sequentially as the needle electrode is advanced toward the neoplastic tissue, or alternatively, advancement of the needle can be stopped at different stages while a plurality of measurements are taken during a measurement period. These measurements are either averaged in the central processor 42 to provide an average signal value for the measurement period or averaged and analyzed in the manner previously described to determine the relationships between the average signal values obtained.

For some applications, it may be desirable to take invasive measurements with a plurality of needle electrodes 130 as illustrated in FIG. 6. Here the electrode array 80 is formed by a plurality of needle electrodes 130 which may or may not be biopsy electrodes. A non-biopsy needle electrode would not include the opening 142 shown in FIG. 7, but would otherwise operate in the same manner as biopsy needle electrode to take internal measurements. The needle electrodes 130 would operate under the control of the switching sequencer 124 in the same manner as described for the electrodes 26a–26d.

The needle electrode and method of the present invention is well adapted for use in conjunction with other diagnostic instruments or procedures. For example, the electrode array 22 may be used for screening in accordance with the discriminant analysis method described to identify and generally locate a possible cancerous lesion, and then the biopsy needle electrode 130 can be used to accurately locate the biopsy needle electrode so that a biospy can be performed. This can be accomplished in conjunction with other procedures, such as radiographic techniques, so that a number of procedures are simultaneously performed to substantiate the results obtained. For example, the discriminant analysis may indicate that a cancerous lesion exists which is confirmed by the biopsy, while the radiographic technique may indicate the location of neoplastic tissue which is confirmed by the use of the biopsy needle electrode 130.

INDUSTRIAL APPLICABILITY

The method and apparatus of the present invention may be employed to effectively screen or diagnose disease states by using skin surface potential taken from a number of different areas on a known or suspected disease site. Malignancy can be indicated with great accuracy while the incidence of false positive diagnosis due to such effects as cases of nonmalignant hyperplasia are minimized. Once an internal disease site has been located, the present invention may be employed to locate a biopsy needle accurately in the diseased tissue at the site. Also, needle electrodes may be used to invasively screen or diagnose diseae states.

We claim:

1. An apparatus for precisely locating suspected neoplastic tissue in a living subject by measuring the electrical potentials which are a function of the electromagnetic fields present within the tissues of the subject in an area where the presence of the neoplastic tissue is suspected consisting essentially of;

reference electrode means adapted for contacting the subject at a reference location, tissue locator electrode means adapted for insertion into the subject's tissues in the area where the presence of the neoplastic tissue is suspected and operative with said reference electrode means to detect the electrical potentials of the electromagnetic fields present between said reference electrode means and said tissue locator electrode means while said tissue locator electrode means is being inserted internally toward and into said suspected neoplastic tissue and to provide test potentials as a function of each of said electrical potentials detected; said tissue locator electrode means including biopsy means for removing a sample of said suspected neoplastic tissue, and processing means connected to said reference electrode means and said tissue locator electrode means and operative to receive said test potentials, said processing means operating to sample a plurality of said test potentials to provide indications which are a function of said test potentials.

2. The apparatus of claim 1 wherein said tissue locator electrode means is a biopsy needle having a pointed end and includes an electrical potential sensing electrode mounted at said pointed end.

3. The apparatus of claim 2 wherein said biopsy needle includes a hollow shaft having a first end and a second end, said electrical potential sensing electrode being formed to provide a point at the first end of said hollow shaft, insulating means mounted on the first end of said hollow shaft between said electrical potential sensing electrode and said hollow shaft to electrically insulate said electrical potential sensing electrode from said hollow shaft, and an opening formed in said hollow shaft at the first end thereof for receiving a sample of the suspected neoplastic tissue.

4. A method of locating suspected neoplastic tissue in a human subject by comparing the differences in electrical potential between the tissues in an area where the presence of neoplastic tissue is suspected including the steps of:

(a) providing a locator electrode for insertion into the tissue of the human subject in the area of the suspected neoplastic tissue;

(b) attaching a reference electrode to a reference area of normal tissue sufficiently proximate to the suspected neoplastic tissue to permit said locator electrode to detect the electrical potentials of the electromagnetic fields present between sad reference and locator electrodes as said locator electrode passes through the tissue of the human subject, (c) inserting said locator electrode and detecting the electrical potentials between said locator electrode and the reference electrode while said locator electrode is being inserted through the tissue into said area of suspected neoplastic tissue; and (d) processing the detected electrical potentials during said locator electrode insertion to determine when the detected electrical potentials reach a value indicative of contact by said locator electrode with neoplastic tissue.

5. The method of claim 4 wherein said locator electrode is mounted on a biopsy needle and includes removing a sample of said neoplastic tissue with said biopsy needle when said locator electrode has contacted said neoplastic tissue.

6. The method of claim 4 which includes detecting the potentials between said locator electrode and reference electrode at a plurality of measurement locations as said locator electrode is inserted through the tissue, comparing the potentials so obtained to identify therefrom a high and a low level potential, and obtaining a differential value indicative of the difference between said high and low level potentials.

7. The method of claim 6 which includes a taking a plurality of potential measurements at each said measurement location, obtaining average potential values for each said measurement location from the measurements taken, comparing said average potential values to identify therefrom high and low level average potentials, and obtaining said differential value from the difference between said high and low level average potentials.

8. The method of claim 4 which includes detecting a plurality of electrical potentials between said reference electrode and said locator electrode after contact by said locator electrode with the neoplastic tissue while maintaining said locator electrode in contact with said neoplastic tissue, comparing the electrical potentials obtained during contact of said locator electrode with said neoplastic tissue to identify a high and low level potential, obtaining a differential value indicative of the difference between said high and low level potentials, and using said differential value to determine the presence or absence of a disease condition.

9. The method of claim 4 which includes detecting a plurality of electrical potentials between said reference electrode and said locator electrode after contact by said locator electrode with the neoplastic tissue while maintaining said locator electrode in contact with said neoplastic tissue, and using said electrical potentials obtained during contact of said locator electrode with said neoplastic tissue to determine the presence or absence of a disease condition.

10. A method for determining the presence of absence of an internal disease condition present at an internal disease site in the area of a test site on a living subject which includes, detecting during a first test period the respective electrical potentials of the electromagnetic field present in said subject between each of a plurality of measurement locations in the area of the test site and at least one reference location on the subject to obtain a representative potential for each measurement for each measurement location during the test period, comparing such representative potentials at the end of the first test period to obtain therefrom relationships which are indicative of either the presence or the absence of the internal disease condition in the area of the test site, inserting a locator electrode into the tissue of the subject in the area of the test site when the presence of the internal disease condition is sensed, detecting the electrical potentials between said reference location and said locator electrode while said locator electrode is being inserted through the tissue toward the internal disease site, and processing the detected electrical potentials during said locator electrode insertion to guide said locator electrode to said internal disease site and to determine when the detected electrical potential is indicative of contact by said locator electrode with said internal disease site.

11. The method of claim 10 wherein said locator electrode is mounted on a biopsy needle and includes removing a sample of neoplastic tissue from said disease site with said biopsy needle when said locator electrode has contacted said neoplastic tissue.

12. An apparatus for precisely locating neoplastic tissue in a living subject by measuring the electrical potentials which are a function of the electromagnetic fields which originate from within and are present on the skin surface of the subject in an area of a potential disease site and are present within the tissues of the subject comprising:

reference electrode means adapted for contacting the subject at one or more reference locations, a plurality of screening electrode means adapted for contact with the skin surface of the subject at spaced locations in the area of the potential disease site and operative with said reference electrode means to detect the potentials of said electromagnetic fields which are present in the area of said potential disease site during a first test period and to provide test signals as a function of the potentials detected, processing means connected to receive said test signals and operative to compare the test signals obtained during said first test period to identify potential relationships indicative of the presence of the neoplastic tissue; and tissue locator electrode means for insertion into the subject's tissues in the area of the potential disease site and operative with said reference electrode means during a second test period to detect electrical potentials of the electromagnetic fields present between said reference electrode means and said tissue locator electrode means while said tissue locator electrode means is being inserted internally toward and into said neoplastic tissue and to provide locator potentials as a function of each of said electrical potentials detected; said processing means being connected to receive said locator potentials and operating to provide indications which are a functions of said locator potentials.

13. The apparatus of claim 12 wherein said processing means operates during said second test period to detect potential changes in said locator potentials as an indicator of when said tissue locator electrode means has reached the neoplastic tissue.

14. The apparatus of claim 12 wherein said processing means is operative during said first test period to receive a plurality of said test signals from a combination of said reference electrode means and said screening electrode means, said processing means being further operative to compare the test signals so obtained to identify a high and low level signal and to obtain a differential value indicative of the difference between said high and low level signals.

15. The apparatus of claim 12 wherein said processing means operates to sample and receive a plurality of said test signals from a combination of each of said screening electrode means and said reference electrode means during said first test period and to average the test signals for each said screening electrode means reference electrode means combinations to obtain an average signal value therefrom, said processing means operating to compare said average signal values obtained for said first test period to identify differential relationships therebetween.

16. The apparatus of claim 15 wherein said processing means operates to compare said average signal values obtained for said first test period and obtain therefrom the maximum and minimum average signal values and subsequently obtaining a differential value indicative of the difference between said maximum and minimum average signal values.

17. The apparatus of claim 16 wherein said processing means operates to compare said differential value to a first reference value, said processing means operating to provide an output indicative of the presence or absence of the neoplastic tissue in accordance with a relationship between said first reference value and said differential value.

18. The apparatus of claim 12 wherein said processing means operates during said second test period to detect the electrical potentials between said locator electrode means and said reference electrode means at a plurality of measurement locations as said location electrode means is inserted toward said neoplastic tissue, said processor means operating to compare the electrical potentials obtained during the second test period to identify therefrom high and low level potential values and to obtain differential values indicative of the difference between said high and low potential values.

* * * * *